United States Patent [19]

Charudattan et al.

[11] Patent Number: 5,393,728
[45] Date of Patent: Feb. 28, 1995

[54] BROAD-SPECTRUM BIOHERBICIDE TO CONTROL SEVERAL SPECIES OF PIGWEEDS AND METHODS OF USE

[75] Inventors: Raghavan Charudattan, Gainesville, Fla.; Yasser A. Shabana, El-Mansoura, Egypt; James T. DeValerio, Starke; Erin N. Rosskopf, Newberry, both of Fla.

[73] Assignee: University of Florida, Gainesville, Fla.

[21] Appl. No.: 77,695

[22] Filed: Jun. 15, 1993

[51] Int. Cl.⁶ ............................................. A01N 63/04
[52] U.S. Cl. ............................................................ 504/117
[58] Field of Search .............................................. 504/117

[56] References Cited

U.S. PATENT DOCUMENTS

| | | | |
|---|---|---|---|
| 3,849,104 | 11/1974 | Daniel et al. | 504/117 |
| 3,999,973 | 12/1976 | Templeton | 504/117 |
| 4,390,360 | 6/1983 | Walker | 504/117 |
| 4,419,120 | 12/1983 | Walker | 504/117 |
| 4,753,670 | 6/1988 | Leth | 504/117 |
| 5,082,489 | 1/1992 | Watson et al. | 504/117 |
| 5,100,456 | 3/1992 | Tsantrizos et al. | 504/117 |
| 5,212,086 | 5/1993 | Watson et al. | 504/117 |

OTHER PUBLICATIONS

Mintz et al. "Factors Influenzing the Biocontrol of Tumble Pigweed (*A. albus*) with *Apospaheria amaranthi*". *Plant Disease* Mar. 1992, pp. 267–269.

Heiny et al. "Redisposition of *A. amaranthi* in Microsphaeropsis". *Mycotaxon*. 44:1 pp. 137–154. Apr.–Jun. 1992.

*Primary Examiner*—Glennon H. Hollrah
*Assistant Examiner*—S. Mark Clardy
*Attorney, Agent, or Firm*—Saliwanchik & Saliwanchik

[57] ABSTRACT

A novel *Phomopsis* sp. fungus is an effective broad-spectrum bioherbicide agent for controlling several economically important pigweed species (*Amaranthus* spp.). The agent is a new species of the plant pathogen *Phomopsis*. Spores and mycelial fragments from the novel fungal species kill many different pigweed biotypes from various parts of the United States and other countries. Various compositions and formulations employing the novel fungus, including its combination with a hydrophilic mucilloid gel, can be used in methods for controlling pigweed.

3 Claims, No Drawings

BROAD-SPECTRUM BIOHERBICIDE TO CONTROL SEVERAL SPECIES OF PIGWEEDS AND METHODS OF USE

This invention was made with government support under Federal Hatch Funds #FLA-PLP-02992. The government has certain rights in this invention.

BACKGROUND OF THE INVENTION

Pigweeds (also called amaranths; Amaranthus spp.) are weeds of worldwide importance in agronomic and horticultural crops. About eight or nine species are economically important in the United States, Canada, Central and South America, Europe, Asia, and Australia. *Amaranthus retroflexus* (redroot pigweed), *A. spinosus* (spiny amaranth), *A. palmeri* (Palmer amaranth), *A. hybridus* (smooth pigweed), *A. tuberculatus* (tall waterhemp), *A. albus* (tumble pigweed), *A. lividus* (livid amaranth), *A. viridus* (slender amaranth), *A. powellii* (Powell amaranth), and other species are among the top ten weeds in several major agronomic and horticultural crops grown in the United States. *Amaranthus hybridus* and *A. retroflexus* are the most troublesome species for most growers. These two species are also regarded as being among the world's eighteen worst weeds.

Currently, chemical herbicides and cultivation are primary means for controlling pigweeds. Although chemical herbicides are generally highly efficacious, they cannot be used in all situations in which pigweeds are a problem. Also, chemical herbicides are disadvantageous in that they are not available for all crops. There are several minor crops affected by pigweeds for which no chemicals are registered due to economic reasons. Perhaps more importantly, pigweed species have developed resistance to several classes of chemical herbicides, and herbicide-resistant pigweeds are a serious problem in many parts of the world. Finally, there is a role for nonchemical alternatives in integrated weed management systems in commercial agriculture and in organic farming systems. These factors make biological control a desirable option.

Three bioherbicides are currently registered for use in North America (DeVine, COLLEGO, and BioMal), and five others are being developed in the United States, Australia, Japan, and Europe. Considerable interest exists for bioherbicide technology, especially for the control of weeds in the specialty or niche markets and for weeds with substantial market sizes. A fungus of the genus Aposphaeria (=Microsphaeropsis) has been described as having limited activity against a narrow range of pigweeds (Mintz, A. S., D. K. Heiny, and G. J. Weidemann (1992) *Plant Disease* 76(3):267–269; Heiny, D. K., A. S. Mintz and G. J. Weidemann, (1992) *Mycotaxon*, XLIV:137–154). However, bioherbicides effective against pigweed are currently unavailable.

Herbicidal metabolites produced by *Phomopsis convolvulus* have been described in U.S. Pat. No. 5,100,456. However, neither the fungus nor its metabolites show activity against pigweeds. *Phomopsis convolvulus* is a distinct species from the novel Phomopsis sp. described herein below and is not known to attack pigweed. Similarly, the *Phomopsis cirsii* described in U.S. Pat. No. 4,753,670 is a distinct fungus from the subject Phomopsis sp. and is not bioherbicidally effective against pigweeds. The Phoma sp. described in U.S. Pat. No. 5,082,498 is clearly different from the subject isolate and is ineffective against pigweed.

A bioherbicide that controls a broad spectrum of pigweed species is therefore highly advantageous. First, there are many specialty crops (fruits, vegetables, ornamentals, and others) that cannot be treated with the available chemicals. Secondly, herbicide-resistant Amaranthus spp. have been reported. A bioherbicide that controls a number of herbicide-resistant pigweeds is an effective tool for resistant weed management programs. Finally, having a bioherbicide that controls many Amaranthus species allows growers who prefer not to use chemical herbicides to combat problematic pigweed infestation.

BRIEF SUMMARY OF THE INVENTION

The subject invention pertains to a novel bioherbicide useful for killing and controlling growth of undesirable pigweed. The bioherbicide comprises a unique and previously undescribed species of the fungus Phomopsis. This new bioherbicide provides several advantages which include, but are not limited to, the following:

1. The novel fungus exhibits lethal effect on several pigweed species; consequently, it can be used against several pigweeds worldwide.

2. The novel fungus can be used in combination with chemical herbicides and other weed management tools to control resistant pigweeds.

3. The novel fungus produces spores or roycelia, both of which have bioherbicidal activity, which results in high efficacy.

4. The novel fungus exhibits rapid disease onset; results indicate bioherbicidal activity after about 18 hours of dew. This can enable the fungus to be used under natural humidity conditions in the field.

5. The novel fungus is compatible for use with psyllium mucilloid (a plant-derived natural hydrophilic polymer) as a formulating agent which enables the fungus to circumvent the need for added dew for infection.

6. The novel fungus exhibits bioherbicidal efficacy against pigweed plants in any and all stages of growth (seedling to post-flowering stages).

7. The novel fungus exhibits high specificity and selectivity for the target weed. The novel fungus did not infect any of 15 non-target crop plants that are commonly grown in the United States.

The subject invention also pertains to a herbicidal composition which can include an effective amount of the novel fungus as an active ingredient formulated with an acceptable agricultural carrier as an inert ingredient. Alternatively, the novel fungus can be formulated in a herbicidal composition with an acceptable agricultural carrier and one or more additional herbicidally active ingredients.

In addition, the subject invention concerns a novel method for the lethal control of a broad spectrum of pigweeds. Essentially, the novel method employs the application of an effective amount of the novel fungus, or composition comprising the novel fungus, to a target pigweed of the genus Amaranthus.

The subject invention further concerns a novel method for compensating for lack of available moisture necessary for certain pathogens to effectively infect a plant. This lack of natural moisture can be a severe limitation in the ability of fungi to infect plants. One aspect of the subject invention is the use of a natural or synthetic mucilloid (hydrophilic polymers) with a biological control agent in order to retain, for prolonged periods, moisture necessary for growth and infection of the biocontrol agent. In a preferred embodiment, the biological control agent is a fungus.

DETAILED DISCLOSURE OF THE INVENTION

The subject invention concerns a novel Phomopsis fungal species and methods of using the novel species to selectively and specifically control the undesired weed, Amaranthus, commonly known as pigweed. A novel composition comprising the novel fungus is also described. Further, a novel formulation using a hydrophilic mucilloid is described, which can be used with other bioherbicides as well.

The fungus grows well at 25°–28° C. on PDA plates. The dense, tan-gray growth sporulates on PDA and oatmeal agar at 23°–28° C. under continuous light (100 $\mu E.m^{-2}.s^{-2}$). The mycelium is septate, branched, hyaline to pale brown. The pycnidia develop on older lesions on dead pigweed tissues, are densely scattered, brownish to black, globose to oblong, ostiolate, and covered by host epidermis. The inner surface is densely covered with conidiophores. Two types of conidia, typical for this genus, are produced in pycnidia. Alpha conidia are hyaline, fusiform, straight, aseptate, and $11-17.6 \times 4.4-6.6\mu$ (av. $14.1 \times 5.7\mu$; mode $13.2 \times 6.6\mu$) in size. Beta conidia are hyaline, filiform, straight or hooked, attenuated, aseptate, and $26.4-28.6 \times 1.1-2.2\mu$ (av. $27.8 \times 1.6\mu$; mode $28.6 \times 1.1\mu$) in size. In addition, this fungus produces a third type of conidia called C-conidia that are uncommon among Phomopsis sp. The C-conidia are $18-22\mu$ in length and slightly curved. Conidiophores are hyaline, phialidic filiform, formed from the inner cells of the locular walls, and occasionally short. Based on these characteristics, the pathogen is identified as a new species of Phomopsis.

The subject Phomopsis sp. was isolated and pure-cultured. Working cultures of this isolate are maintained at 9° C. on PDA slants. A culture containing the fungus of the subject invention was deposited on May 25, 1993 with the American Type Culture Collection (ATCC), 12301 Parklawn Drive, Rockville, Md. 20852 USA. The culture was assigned accession number ATCC 74226 by the repository.

The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are fled. However, it should be understood that the availability of a deposit does not constitute a license to practice the subject invention in derogation of patent fights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The novel bioherbicide can be utilized effectively in diverse formulations, including the agronomically acceptable adjuvants and carriers normally employed for facilitating the dispersion of active ingredients for agriculture applications recognizing a known fact that the dosage, formulations, mode of application of a chemical agent, and other variables may affect its activity in any given application. Thus, the described bioherbicide can be formulated as a suspension or dispersion, in aqueous or non-aqueous media, as a dust, as a wettable powder, as an emulsifiable concentrate, as a granule, or as any of several other known types of formulations, depending on the desired mode of application. These herbicide compositions can be applied as sprays, dust, or granules directly to the plant or its situs where herbicidal activity is desired. In a preferred embodiment, described in more detail below, the fungus of the subject invention is formulated with a moisture retaining component.

The subject fungus, Phomopsis sp., can most preferably be obtained by conventional culture techniques from the deposited culture specimens. To convert it to a form which will facilitate the preparation of the following described compositions, a slurry can be prepared which can then be dried onto a primary agronomically acceptable carrier, e.g., vermiculite, whereby the fungus is adsorbed onto the carrier. If desired, the slurry can be used as the concentrate for the herbicidal composition. The actual concentration of propagules in the formulated composition is not particularly critical, and is a function of practical considerations such as the properties of the vehicle or carrier, and the method of application. Certain spore concentrations, which are described herein, however, have been found to be preferred. For purposes of formulation and application, an "effective amount" is defined to mean any such quantity of propagules sufficient to infect the target plant and thereby induce the lesions involved in the lethal activity described herein.

The subject material described herein can be applied to a region to be treated by being applied directly to the soil as pre-emergence treatment or as post-emergence treatment to plant foliage, or they can be mixed intimately with the soil. The preferred mode of treatment is application after emergence of the plant foliage. The subject materials described herein can, for example, be applied to soil or plant foliage in amounts of from about 100 g to 100 kg per hectare.

In order to provide compositions in the form of dust, granules, water dispersible powders, aqueous dispersions, or emulsions and dispersions in organic liquids, the carrier or diluent agent in such formulations may be a finely divided solid, an organic liquid, water, a wetting agent, a dispersing agent, humidifying agent, or emulsifying agent, or any suitable combination of these. Generally, when liquids and wettable powders are prepared, a conditioning agent comprising one or more surface-active agents or surfactants is present in amounts sufficient to render a given composition containing the active material, the microorganism, dispersible in water or oil. The preferred liquid carrier is water, and the spore concentrate is dispersed to make a concentration of from about $1 \times 10^4$ to about $1 \times 10^8$ spores/ml.

The surface active agent used in the invention can be a wetting, dispersing, or emulsifying agent which will assist dispersion of the effective composition. The surface-active agent or surfactant can include such anionic, cationic, and non-ionic agents as have heretofore been generally employed in plant control compositions of similar type. Suitable surface-active agents are set forth, for example, in "Detergents and Emulsifiers" 1971 Annual by John W. McCutcheon, Inc.

In general, 1-10% by weight of the surface-active agent can be used in compositions of this invention and ordinarily the amount of surface-active agent will range from 1-5% but may even be less than 1% by weight.

Additional surface-active agents can be added to formulations to increase the ratio of surfactants:active ingredients up to as high as 5:1 by weight. Such compositions may have a greater biological effectiveness than can be expected when the components are used separately. When used at higher ratios, it is preferred that the surfactant be present in the range of one-fifth to five parts surfactant for each one part of active agent.

In a preferred formulation, the subject Phomopsis sp. can be formulated with a moisture-retaining agent such as a hydrophilic polymer, e.g., the natural, plant-derived mucilloid, psyllium mucilloid. The term "mucilloid," as used herein, is readily apparent to persons of ordinary skill in the art to mean or refer to any of several plant-derived, water-soluble substances having the ability to retain moisture by, for example, preventing run-off or slowing the evaporation process. Mucilloids are hydrophilic compounds which are well known and recognized in the art to form a gel when mixed with a liquid, especially water or other aqueous liquid. A suitable mucilloid which can be used for purposes of the subject invention is that which is derived from psyllium. Psyllium mucilloid is commonly sold as the laxative, Metamucil. Examples of other hydrophilic gels which can be employed are gellan gum, xanthum gum, and cellulosic gels.

A formulation employing psyllium mucilloid advantageously facilitates infectivity and increases the bioherbicidal activity of the fungus. In addition, a bioherbicidal formulation comprising the novel Phomopsis sp. and psyllium mucilloid advantageously eliminates or reduces the need for a dew period. Advantageously, other hydrophilic gels can be used to maintain moisture levels and promote plant infection when applied in the presence of fungi. The mucilloid can be applied either before or after the fungal pathogen. Preferably, the fungus and hydrophilic mucilloid gel are applied contemporaneously or approximately simultaneously. Most preferably, the fungal pathogen and mucilloid can be formulated together and applied as a composition.

Further, the mucilloid can be used in combination with other biocontrol agents including, but not limited to, other pathogenic fungi, such as *Alternaria cassiae* and *Alternaria eichhorniae*.

Spores of the novel Phomopsis sp. can be mixed with those of *Alternaria cassiae* to enlarge the scope of control of undesirable vegetation. For example, this mixture can be used to control both pigweed and sicklepod (*Cassia obtusifolia*), two troublesome weeds in the Southeast. Further, spores of the subject Phomopsis sp. can be mixed with those of *A. cassiae* to control pigweed and coffee senna. The use of *A. cassiae* to control sicklepod, showy crotolaria, and coffee senna is disclosed in U.S. Pat. No. 4,390,360, which is incorporated herein by reference thereto. The culture, means of growing, and application to those weeds disclosed in U.S. Pat. No. 4,390,360 can be used herein. Mixtures of Phomopsis sp., ATCC 74226, and *A. cassiae*, for example, *A. cassiae* NRRL 12533, can be made by methods well known in the art, utilizing the disclosure of U.S. Pat. No. 4,390,360 and that contained herein.

Spores are the preferred form for bioherbicidal use of the novel fungus; however, the subject fungus can also be formulated as fragmented mycelia and applied in foliar sprays. The fungal propagules including the spores (conidia) and mycelia can be mass-produced for field inoculations by culturing the subject Phomopsis sp. on half-strength Emerson's yeast-starch agar as shown in Table 1, below. Spores or mycelia of this fungus, both of which we can produce easily and abundantly in culture, can be used to create high levels of disease and weed kill. This provides great latitude in the production of inoculum for bioherbicide formulations.

TABLE 1

| Emerson's yeast-starch agar | |
|---|---|
| Nutrient | Concentration (g/L) |
| Powdered yeast extract (Difco) | 2 |
| Soluble starch | 7.5 |
| $K_2HPO_4$ | 0.5 |
| $MgSO_4.7H_2O$ | 0.25 |
| Distilled water | |

The propagules can be incorporated into compositions suitable for field application. They can be used with any liquid vehicle or solid carrier as described. Both the spores and the roycelia lend themselves to formulation as liquid sprays and wettable powders for post-emergence treatment. They can also be formulated as controlled-release granules for pre-emergence weed control. Infection is promoted in the presence of free moisture (dew) for a period of at least about 12 hours. At a temperature of 25° C., the optimal moisture period is 16 to 20 hours. Infection is also promoted in the absence of added dew when psyllium mucilloid is used with the inoculum.

Spores or mycelial fragments of the novel Phomopsis sp. can be combined with various chemical additives, particularly chemical herbicides, to increase weed control. An example of some effective chemical herbicides are 2,4-D, atrazine, linuron, paraquat, alachlor, metolachlor, glyphosate, dichlobenil, EPTC, and arsenicals. These additives would be expected to broaden the spectrum of activity so that additional species of weeds can be controlled. Application rates of these chemicals would be expected to be less than or equal to the rates recommended for conventional use.

Following are examples which illustrate procedures, including the best mode, for practicing the invention. These examples should not be construed as limiting. All percentages are by weight and all solvent mixture proportions are by volume unless otherwise noted.

EXAMPLE 1

Efficacy of the Novel Isolate Against a Broad Spectrum of Pigweeds

The fungus was screened in the greenhouse for pathogenicity to 39 pigweed biotypes belonging to 22 species and alligatorweed (*Alternanthera philoxeroides*). Two sets of trials were conducted to show the bioherbicide activity of the novel Phomopsis sp. In the first set of trials, the plants were inoculated with a blended mixture of mycelium and conidia (2 to $3.55 \times 10^6$ ml; sprayed to runoff) obtained from agar-plate cultures. Metamucil (0.5%) was added to the inoculum suspension, and the inoculated plants were incubated for 24 hours in the dew chamber before placing them in the greenhouse. Control plants were sprayed with a suspension of Metamucil only and treated similarly.

In the second set of trials, the plants were inoculated with $1 \times 10^6$ conidia per ml plus 0.05% Triton X-100 surfactant was-used (sprayed to runoff) and the treated plants were incubated in the dew chamber for 24 hours.

All major weedy pigweeds and amaranths were tested, and the results are shown in Table 2. Many of the biotypes were completely killed by the fungus. For some biotypes, although severely diseased, less than 100% of the plants were killed. Alligatorweed, an important aquatic weed, was immune. Advantageously, the certain crop plants, including three varieties of squash, two varieties of spinach, beets, cucumber, cantaloupe, okra, carrots, beans, mustard, onion, corn, and sunflower are immune to the novel Phomopsis sp. These results demonstrate that Phomopsis sp. can be an effective and selective bioherbicide for control of Amaranthus spp.

TABLE 2

Effect of Phomopsis sp. on plant species tested

| Species | Origin | % Showing symptoms | % Dead |
|---|---|---|---|
| Alternanthera philoxeroides* | USA-FL | 0 | 0 |
| Amaranthus acutilobus* | Germany | 100 | 100 |
| A. albus | Germany | 100 | 45 |
| A. australis | USA-FL | 31 | 0 |
| A. australis | USA-FL | 39 | 0 |
| A. blitoides* | Germany | 100 | 0 |
| A. caudatus | Argentina | 100 | 11 |
| A. caudatus | USA | 100 | 28 |
| A. crassipes | Czechoslovakia | 100 | 17 |
| A. cruentes | Mexico | 100 | 0 |
| A. cruentus | USA-AR | 100 | 22 |
| A. cruentus | USA-ME | 100 | 0 |
| A. cruentus | Mexico | 100 | 17 |
| A. delflexus | Germany | 100 | 42 |
| A. dubius | Ghana | 100 | 6 |
| A. dubius | Jamaica | 100 | 6 |
| A. floridanus | USA-FL | 23 | 0 |
| A. graecizans | USA-IA | 100 | 12 |
| A. hybridus | Argentina | 100 | 0 |
| A. hybridus | Ecuador | 100 | 62 |
| A. hybridus | USA-PA | 100 | 0 |
| A. hybridus | Zimbabwe | 84 | 0 |
| A. hypochondriacus | Mexico | 89 | 6 |
| A. lividus | Hong Kong | 100 | 84 |
| A. lividus | India | 95 | 50 |
| A. palmeri | USA-AR | 72 | 6 |
| A. palmeri | Senegal | 84 | 0 |
| A. powellii | Germany | 100 | 84 |
| A. powellii | USSR | 100 | 84 |
| A. quintensis | Ecuador | 100 | 50 |
| A. retroflexus | India | 100 | 45 |
| A. retroflexus | USA-IA | 100 | 12 |
| A. rudis | USA-IA | 67 | 12 |
| A. spinosus* | Indonesia | 100 | 28 |
| A. spinosus | Zimbabwe | 100 | 0 |
| A. tricolor | India | 100 | 50 |
| A. tricolor | USA | 78 | 28 |
| A. tricolor | USA | 67 | 34 |
| A. viridus | Indonesia | 100 | 59 |
| A. viridus | Unknown | 100 | 78 |

Results were recorded five weeks after plants were inoculated. Average of two trials, each with three replicates, except species with astericks which were tested only once.

EXAMPLE 2

Pathogenicity of the Novel Isolate

The subject isolate was confirmed to be the incitant of the observed lethal effect. The lethal process progressed rapidly from the time of inoculation with spore or mycelium cultures of the subject isolate. Lesions were observed on the lower leaves 12 days after inoculation; two days later they extended to the upper leaves. Stems and petioles exhibited lesions within or soon after 3 weeks following inoculation. The lesions appeared on both surfaces of pigweed leaves as chlorotic flecks, which developed to brown, circular or irregular necrotic spots. These spots enlarged and darkened at the margins with light brown center which, in some instances, abscised leaving a shot-hole. Eventually, the necrotic lesions coalesced, causing blight over most of the leaf area. Necrotic lesions extended to and killed the petioles, which produced premature leaf abscission. On stems, the lesions appeared as prolonged, dark brown to black necrotic areas which caused stem girdling, and eventual death of the entire plant. Results of experiments conducted under controlled conditions confirm that there are no major epidemiological limitations to the lethal activity of the subject isolate.

EXAMPLE 3

Production of Spores for Inoculum

To produce spores for bioherbicidal use, culture plates inoculated with the subject isolate were sealed with Parafilm and incubated for several weeks at $25°\pm2°$ C. under continuous light supplied by two 40-w cool-white fluorescent lamps suspended 45 cm above plates (37 $\mu E.m^{-2}.s^{-1}$). The cultures were then flooded with 10 ml of sterile deionized water and the spores were dislodged by thoroughly rubbing the agar surface. Plates were washed three times and the spore suspension was filtered through a piece of nylon cloth (mesh diam. 102$\mu$). Concentrations of spore suspensions ranging between $5\times10^5$ and $5\times10^7$ spores/ml were made from the stock suspension. Specifically, five concentrations of inoculum were used: $6.25\times10^5$, $1.25\times10^6$, $2.5\times10^6$, $5\times10^6$, and $1\times10^7$ spores/mi. The psyllium mucilloid, Metamucil, (Procter & Gamble, Cincinnati, Ohio) was added to each spore suspension (0.5% w/v). The plants were inoculated by swabbing the leaves and stems with the inoculum. Alternatively, the suspensions could be sprayed with a hand-held garden sprayer. Plants were then placed in a dew chamber for 18 hours in the dark at 28° C. and 100% relative humidity, and then transferred to the greenhouse at 20°–30° C. Control plants were painted with 0.5% psyllium mucilloid suspension and maintained under identical conditions as above. From the lesions that appeared on the treated plants, the inoculum densities of $2.5\times10^6$ to $1\times10^7$ were determined to be the preferable densities to induce plant kill. Younger plants were more susceptible to the disease than were older plants.

EXAMPLE 4

Efficacy of Mycelial Fragments

Mycelial fragments as well as spores are suitable for initiating high levels of herbicidal activity against pigweed. For inoculum, the fungus was grown on PDA plates at 25° C. under continuous darkness for 2 weeks. Mycelial growth from three 9-cm plates was scraped off and comminuted for 9 seconds in 100 ml of sterile deionized water in a Waring blender. To the blended suspension, 0.5% (w/v) psyllium hydrophilic mucilloid, e.g., Metamucil was added as a gelling agent. Ten individual pigweed plants (*A. retroflexus*), which had been transplanted 3–4 weeks after seeding and maintained in 12-cm day pots, were inoculated 3–4 weeks post transplantation. Plants were inoculated by brushing the inoculum gel with an artist brush on leaf and stem surfaces till runoff. Controls were painted with Metamucil gel (0.5% w/v in water) only. Plants were then placed in a dark dew chamber at 28° C. for 20 hours before moving to a greenhouse bench at 20°–30° C. for the following 8 weeks.

EXAMPLE 5

Bioherbicidal Formulation Using Mucilloid

Psyllium mucilloid was used in an inoculum consisting of $1 \times 10^6$ conidia obtained from V-8 agar plates. A lower concentration of Metamucil, 0.05%, and A. hybridus were used. Four treatments were evaluated: (1) inoculum+Metamucil+24 hours incubation in a dew chamber; (2) Metamucil suspension only+dew; (3) inoculum+Metamucil, without dew (plants placed directly in the greenhouse after application of the inoculum); and (4) Metamucil only, without dew. Disease symptoms appeared on plants treated with (1) and (3), but not on those treated with (2) and (4) (no fungus). The appearance of symptoms on treatment (3) confirmed the ability to cancel the need for maintaining the plants under prolonged dew in a dew chamber.

EXAMPLE 6

Other Bioherbicidal Formulations

A. Wettable powders. Wettable powders are water-dispersable compositions containing the active material, an inert solid extender, and one or more surfactants to provide rapid wetting and to prevent heavy flocculations when suspended in water.

The inert extenders which are preferred for use in the wettable powders of this invention containing the active compounds are of mineral or organic origin.

Extenders suitable for the wettable powder formulations of this invention are the natural clays, vermiculite, diatomaceous earth, and synthetic mineral fillers derived from silica and silicate. Most preferred filters for this invention are kaolinites, attapulgite clay, montmorillonite clays, synthetic silicas, synthetic magnesium silicate, and calcium sulfate dihydrate. A surface active agent can also be added to give a homogenous and stable formulation.

Among the more preferred surfactants are the non-ionic and anionic types. They are most suitable for the preparation of dry, wettable products of this invention and dispersants. Occasionally a liquid, non-ionic compound which is primarily an emulsifier may serve as both wetter and dispersant.

Most preferred wetting agents are alkylbenzene and alkylnaphthalene sulfonates, sulfated fatty alcohols, amines, or acid amides, long chain esters of sodium isethionate, esters of sodium sulfosuccinate, sulfated or sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalene sulfonates, polymethylene bisnaphthalene sulfonate, and sodium-N-methyl-N-(long chain acid) taruates.

Wetting and dispersing agents in these preferred wettable powder compositions of the invention are usually present at concentrations of from about 0.5 weight percent to 5 weight percent. The inert extender then completes the formulation. Where needed, 0.1 weight percent of the extender may be replaced by a corrosion inhibitor or an anti-foaming agent or both.

Thus, wettable powder contains a corrosion inhibitor or an anti-foaming agent or both, the corrosion inhibitor should not exceed about 1 percent of the composition, and the anti-foaming agent should not exceed about 0.5 percent by weight of the composition, both replacing equivalent amounts of the inert extender.

B. Dusts. Dusts are dense powder compositions which are intended for application in dry form. Dusts are characterized by their free-flowing and rapid settling properties so that they are not readily windborne to areas where their presence is not desired. They contain primarily an active ingredient and a dense, free-flowing, solid extender. Their performance is sometimes aided by the inclusion of a wetting agent and convenience in manufacture frequently demands the inclusion of an inert absorptive grinding aid.

The wettable powder as described above can also be used in the preparation of dusts. While such wettable powders can be used directly in dust form, it is more advantageous to dilute them by blending with the dense dust diluent. In this manner, dispersing agents, corrosion inhibitors, and anti-foam agents may also be used as components of a dust.

Thus, the dust compositions of this invention can comprise from about 0.5 to 20.0 weight percent active ingredient, 5 to 25 weight percent filler, 0.0 to 1.0 weight percent wetting agent, and from about 30 to 90 weight percent dense, free-flowing extender, as these terms are used herein. Such dust formulations can contain, in addition, minor amounts of dispersants, corrosion inhibitors, and anti-foam agents derived from the wettable powders used to make the dust.

C. Emulsifiable oils. Emulsifiable oils are usually solutions or suspensions of active material in non-water miscible solvents together with a surfactant and/or emulsifier.

For compositions of this invention, emulsifiable oil compositions can be made by mixing the active ingredient with an organic solvent and surfactant. Suitable solvents for the compositions of this invention are chlorinated solvents, water immiscible ethers, esters, or ketones alone or in admixture with aromatic hydrocarbons. Suitable surfactants are those ionic or non-ionic agents known to the art as emulsifying agents.

Emulsifying agents most suitable for the emulsifiable oil compositions of this invention are long chain alkyl or mercaptan polyethoxy alcohols, alkylaryl polyethoxy alcohols, sorbitan fatty acid esters, polyoxyethylene ethers with sorbitan fatty acid esters, polyethylene glycol esters with fatty rosin acids, fatty alkylol amide condensates, calcium and amine salts of fatty alcohol sulfates, oil soluble petroleum sulfonates, or preferably mixtures of these emulsifying agents should comprise from about 1 to 10 weight percent of the total composition. As described above, however, up to 5 parts of emulsifying agent for each part of active ingredient can be used.

Thus, emulsifiable oil compositions of the present invention can consist of from about 10 to 50 weight percent active ingredient, about 40 to 82 percent solvents, and about 1 to 10 weight percent emulsifier, as these terms are defined and used above.

D. Granules. Granules are physically stable, particulate compositions containing spores and/or mycelia of this invention which adhere to or are distributed through a basic matrix of a coherent, inert carrier with microscopic dimensions. In order to aid leaching of the active ingredient from the granule, a surfactant can be present.

The inert carrier is preferably of mineral origin, and suitable carriers are natural clays, some pyrophyllites and vermiculite. Suitable wetting agents can be anionic or non-ionic.

For the granule compositions of this invention, most suitable carriers are to two types. The first are porous, absorptive pre-formed granules, such as preformed and screened granular attapulgite or heat expanded, granular, screened vermiculite. On either of these, a solution of the active agent can be sprayed and will be absorbed at concentrations up to 25 weight percent of the total weight. The second type are initially powdered kaolin clays, hydrated attapulgite, or bentonite clays in the form of sodium calcium, or magnesium bentonites. Water-soluble salts such as sodium salts may also be present to aid in the disintegrations of the granules in the presence of moisture. These ingredients are blended with the active component distributed uniformly throughout the mass. Such granules can also be made with 25 to 30 weight percent active component but more frequently a concentration of about 10 weight percent is desired for optimum distribution. The granular compositions of this invention are believed to be most useful in a size range of 15–30 mesh.

The most suitable wetting agents for the granular compositions of this invention depend upon the type of granule used. When pre-formed granules are sprayed with active material in liquid form, the most suitable wetting agents are non-ionic, liquid wetters miscible with the solvent. These are more generally known in the art as emulsifiers and comprise alkylaryl polyether alcohols, alkyl polyether alcohols, polyoxethylene sorbitan fatty acid esters, polyethylene glycol esters with fatty or rosin acids, fatty alkylol amide condensates, oil petroleum or vegetable oil sulfonates, or mixtures of these. Such agents will usually comprise up to about 5 weight percent of the total composition.

When the active ingredient is first mixed with a powdered carrier and subsequently granulated, liquid non-ionic wetters can still be used, but it is usually preferable to incorporate at the mixing stage one of the solid, powdered anionic wetting agents such as those previously listed for the wettable powders. Such agents should comprise about 0 to 2 percent of the total composition.

Thus, the preferred granular formulation of this invention comprises about 5 to 30 weight percent active material, about 0 to 5 weight percent wetting agent, and about 65 to 95 percent inert mineral carrier, as these terms are used herein.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A herbicidal composition comprising an effective mount of a substantially pure isolate of a Phomopsis fungal species and an acceptable agricultural carrier, said Phomopsis isolate having all the identifying characteristics of culture deposit ATCC 74226, wherein said composition is a formulation comprising a psyllium mucilloid hydrophilic gel.

2. The herbicidal composition, according to claim 1, wherein one of said identifying characteristics is activity against an amaranth.

3. A method for controlling an Amaranthus weed comprising applying an effective amount of a substantially pure isolate of a Phomopsis fungus, wherein said Phomopsis has all the identifying characteristics of culture deposit ATCC 74226, wherein said composition is a formulation comprising a psyllium mucilloid hydrophilic gel.

* * * * *

UNITED STATES PATENT AND TRADEMARK OFFICE
CERTIFICATE OF CORRECTION

PATENT NO. : 5,393,728
DATED : February 28, 1995
INVENTOR(S) : Raghavan Charudattan, Yasser A. Shabana, James T. DeValerio, and Erin N. Rosskopf It is certified that error appears in the above-indentified patent and that said Letters Patent is hereby corrected as shown below:

Column 2, line 27: Delete "roycelia" and insert --mycelia--.

Column 3, line 50: Delete "fled" and insert --filed--.

Column 6, line 29: Delete "roycelia" and insert --mycelia--.

Column 6, line 65: Delete "(2 to 3.55 x 106 ml;" and insert --(2 to 3.55 x $10^6$ ml;--.

Column 7, line 6: Delete "was-used" and insert --was used--.

Column 8, line 68: Delete "day" and insert --clay--.

Column 10, line 4: Delete "should-not" and insert --should not--.

Signed and Sealed this

Fourth Day of July, 1995

BRUCE LEHMAN

*Attest:*

*Attesting Officer*     *Commissioner of Patents and Trademarks*